United States Patent [19]

Nicol

[11] Patent Number: 4,897,927
[45] Date of Patent: Feb. 6, 1990

[54] ELECTRICAL ANGULAR DISPLACEMENT SENSOR

[75] Inventor: Alexander C. Nicol, Glasgow, Scotland

[73] Assignee: University of Strathclyde, Glasgow, Scotland

[21] Appl. No.: 948,347

[22] PCT Filed: Aug. 30, 1985

[86] PCT No.: PCT/GB85/00387
§ 371 Date: Dec. 1, 1986
§ 102(e) Date: Dec. 1, 1986

[87] PCT Pub. No.: WO86/01588
PCT Pub. Date: Mar. 13, 1986

[30] Foreign Application Priority Data

Sep. 1, 1984 [GB] United Kingdom ............. 8422136

[51] Int. Cl.$^4$ .................................................. A61B 5/10
[52] U.S. Cl. ............................................. 33/534; 33/512; 33/DIG. 13
[58] Field of Search ............. 33/512, 534, 544, 1 N, 33/1 PT, DIG. 13; 128/2 S; 338/47

[56] References Cited

U.S. PATENT DOCUMENTS

| | | | |
|---|---|---|---|
| 2,885,524 | 5/1959 | Eisler | 338/2 X |
| 3,305,816 | 2/1967 | Doi | 338/2 |
| 3,854,112 | 12/1974 | Greenwood | 338/47 |
| 3,991,745 | 11/1976 | Yoslow | 33/512 X |

FOREIGN PATENT DOCUMENTS 0115620 8/1984 European Pat. Off. .
825448 12/1937 France ................................. 33/403

Primary Examiner—Harry N. Haroian
Attorney, Agent, or Firm—Sixbey, Friedman, Leedom and Ferguson

[57] ABSTRACT

The sensor has at least one strain gauge secured to a strip sufficiently flexible to bend without permanent plastic deformation through a small radius. The output is directly proportional to the relative angular orientation of the ends of the strip regardless of the orientation intermediate the ends.

9 Claims, 2 Drawing Sheets

ELECTRICAL ANGULAR DISPLACEMENT SENSOR

This invention relates to an electrical sensor for measuring angular displacement. Particularly, but not exclusively, the invention relates to an electro-goniometer for use in monitoring joint mobility in patients with ailments such as arthritis which produce abnormal joint movement.

One electro-goniometer for use in medical assessment of joint mobility uses mercury-filled tubes as resistive elements of a Wheatstone bridge circuit. Two or four such tubes are used to provide a bendable beam and a linear relationship between electrical output and angular displacement is given. Problems have been encountered concerning the long-term stability of the electrode/mercury interface and also the well-recognised toxicity of mercury makes its use undesirable.

Another known type of electro-goniometer for orthopaedic diagnosis uses an electrically conductive impregnated plastics strip. Although this arrangement allows a small flexible unit to be made great difficulties with the calibration and electrical stability have been encountered.

An object of this invention is to obviate or mitigate the aforesaid disadvantages.

According to the present invention there is provided an electrical sensor for use in providing a signal indicative of angular displacement between two spaced locations, comprising a flexible carrier of material capable of flexing without permanent plastic deformation when its ends are fixed to said locations and said locations undergo relative rotary movement within a predetermined range; and at least one electrically conductive element having a resistance which is a function of strain affixed to the carrier and extending therealong substantially the whole distance between said locations.

Preferably the carrier is a thin strip of spring steel not exceeding 0.5 mm in thickness. Other possible materials are, for example, non-ferrous metals, acrylic polymers, thermoplastics materials and other plastics materials and fibres.

The strain may be monitored by measuring the electrical resistance of the gauges in a Wheatstone bridge arrangement.

The electrical output may be calibrated to read angular displacement between the ends of the carrier.

The criteria employed in producing the electro-goniometer of this invention were to produce a device which:
(a) required no special alignment with the rotation axis of the limbs,
(b) had low stiffness to facilitate fixation to limbs,
(c) was small enough to be worn beneath a patient's clothing,
(d) has long term electrical stability, and
(e) has infinitely variable electrical output.

The electro-goniometer of the invention uses the 'bending beam' approach but replaces the mercury filled tubes of prior devices, suitably with commercially available strain gauges. These gauges have a definite strain limit and have, up till now, been used to measure strain, stress or force where no appreciable angular displacements have occurred. The use of strain gauges where significant deflections would take place is a rather controversial step but the strain magnitude has been reduced sufficiently by decreasing the thickness of the bending beam to very small values.

The resulting device is therefore very flexible and tests have shown the electrical output to be linearly related to angular movement and stability to be excellent. In addition, the method of bending does not influence the output (a Z bend would zero if the top and bottom ends of the carrier were parallel). The size of the unit can be very small and will therefore easily satisfy the criterion of being worn beneath clothing. The device therefore oversomes several of the limitations of previous devices and is convenient for the measuring of joint motion in clinical and research centres.

The mechanics involved in the design of the bending beam originate from the equation for pure bending:

$$\frac{\sigma}{y} = \frac{M}{I} = \frac{E}{R}$$

where
$\sigma$ = stress in a particular fibre (usually surface)
Y = distance from neutral axis of beam to the fibre in question
M = Bending moment applied to beam
I = Moment of intertia of beam (geometry)
E = Young's Mondulus of Elasticity for material
R = Radius of curvature of deformed beam For the use of a bending beam as an electro-goniometer it is preferable to have zero bending moment (or resistance to bending movement) therefore the equation:

$$\frac{\sigma}{y} = \frac{E}{R}$$

is used giving $$\sigma = \frac{Ey}{R}$$

Since the strain gauges measure the strain (change in length divided by the original length) is it necessary to relate stress ($\sigma$) to strain ($\epsilon$) using Youngs Modulus:

$$\sigma = \epsilon E$$

The bending equation therefore reduces to $$\epsilon E = \frac{Ey}{R}$$

$$\epsilon = \frac{y}{R}$$

In other words the surface strain of a bending beam is directly related to the thickness (2y) and inversely related to the radius of curvature of the deflected beam. For normal strain gauges the limit of strain will be in the order of a few thousand microstrain (i.e. 1000-10,000×10$^{-6}$). An example of the scale of strain means that a beam 5 mm thick cannot bend tighter than a 250 mm radius arc without the danger of plastic deformation.

$$R = \frac{y}{\epsilon} = \frac{2.5}{10 \times 10^{-3}}$$
$$= 250 \text{ MM}$$

For normal operating conditions a working strain of $1000 \times 10^{-6}$ is ideal which would result in a radius of curvature of 2.5 m for a 5 mm thick beam.

For use as a flexible electro-goniometer for joint assessment the bending beam must be able to conform to a much smaller radius of curvature. Values as low as 5 mm are required in some operating conditions which means the thickness of the beam must be recalculated.

$$\epsilon = \frac{Y}{R}$$

$$Y = \epsilon R = (1000 \times 10^{-6}) \times 5 \text{ mm}$$
$$= 5 \times 10^{-3} \text{ mm}$$
$$= 0.005 \text{ mm } (0.01 \text{ mm thickness})$$

This value is extremely small and for practical limits of thickness of shim to 0.05 mm results in larger strains or larger radii of curvature. Alternatively a bend of 50 mm radius would suit a 0.05 mm shim.

Embodiments of the invention will now be described, by way of example, with reference to the accompanying drawings, in which.

Figure 1:
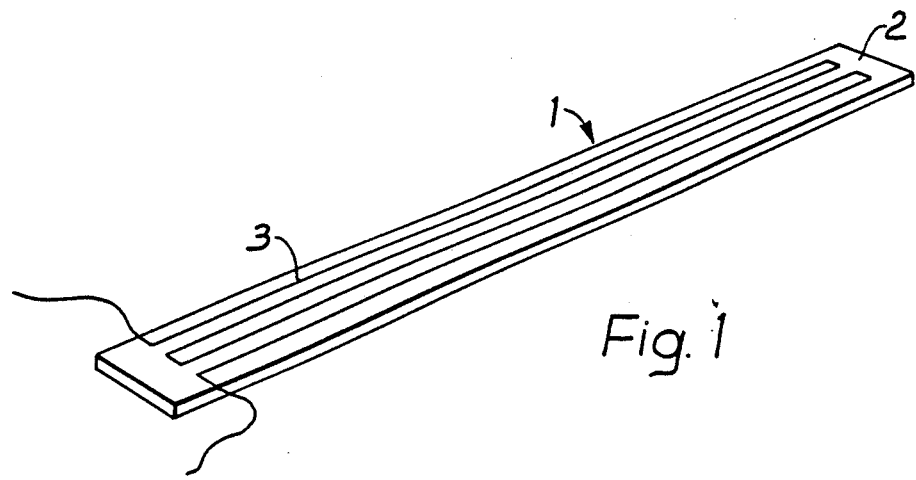
FIG. 1 is a schematic perspective view of a device embodying the invention.

Referring to FIG. 1, an electro-goniometer 1 comprises an elongate carrier strip 2 of spring steel having an elongate strain gauge 3 adhesively secured thereto and aligned with the longitudinal axis of the strip 2. The strain gauge 3 extends along substantially the whole length of the carrier strip 2. Any commercially available strain gauge of suitable dimensions may be used; examples are strain gauges sold as Kyowa KC-120-Al-11 and Showa N.11-FA-60-120-11. The strip 2 in this embodiment has the following features:

| | |
|---|---|
| Length | 125 mm |
| Width | 4 mm |
| Thickness | 0.05 mm |
| Material | High carbon steel |

A second, similar strain gauge is preferably provided on the opposed face of the strip 2.

Figure 2:
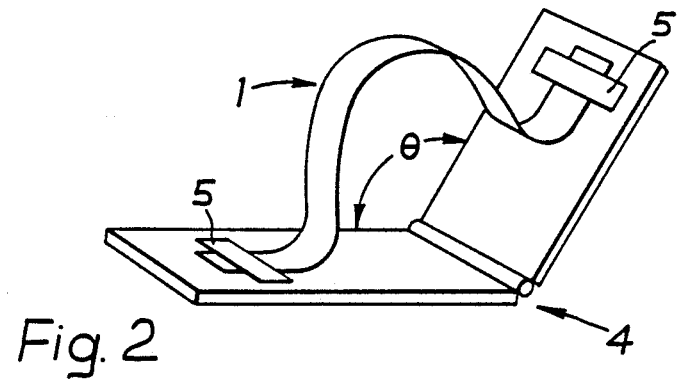
FIG. 2 is a perspective view showing a device according to the invention applied to a hinged joint.

FIG. 2 shows the device 1 applied to a hinged joint 4 capable of relative rotation to give a variable angle $\theta$. The joint 4 is shown for simplicity as a pair of plates hinged together, but in practice could be for example an ankle joint. The device 1 is secured at its ends by any suitable means, such as adhesive tape 5. On any convex curve of the strip 2 the strain gauge 3 is stretched and thus its resistance rises, while any concave curvature produces a reduction in resistance. The net change in resistance is thus a function of the angle $\theta$, regardless of the curvature or number of curves intermediate the ends of the goniometer 1.

Figure 3:
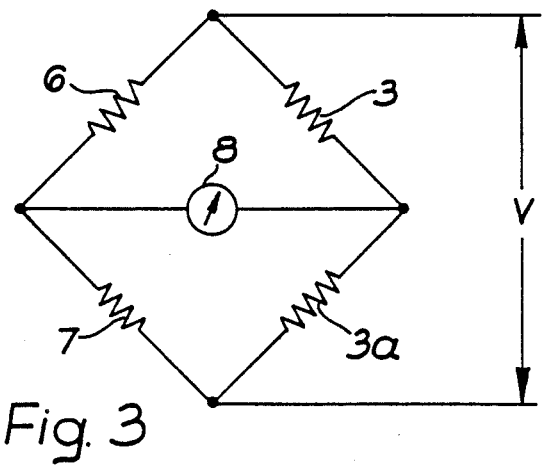
FIG. 3 shows a circuit incorporating the device.

FIG. 3 illustrates one circuit suitable for use with the present invention. A goniometer 1 having series front and rear strain gauges 3, 3a is connected in a bridge circuit with resistors 6, 7. Further resistors and/or amplifiers may be included in the bridge to improve sensitivity. The resistors 6, 7 may be fixed resistors in a monitoring circuit, or alternatively may comprise further strain gauges adjacent the goniometer to provide compensation for ambient conditions such as temperature. It is also possible to provide all four arms of the bridge as strain gauges on a single carrier.

Figure 4:
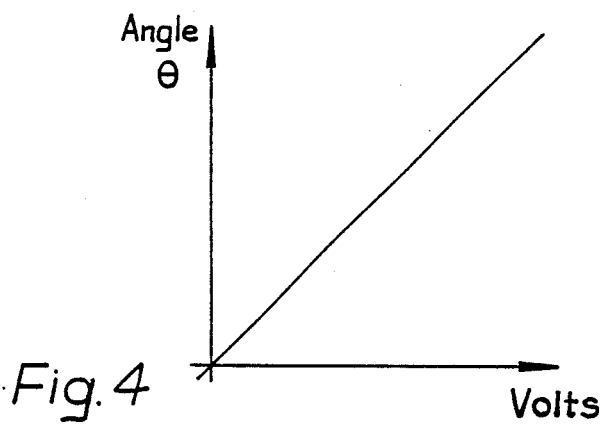
FIG. 4 is a typical calibration graph.

As seen in FIG. 4 the voltage measured across the goniometer of the invention is linearly proportional to the angle $\theta$ between its ends. Thus a meter such as 8 (FIG. 3) can readily be calibrated to give a reading directly in angular measurement.

Figure 5:
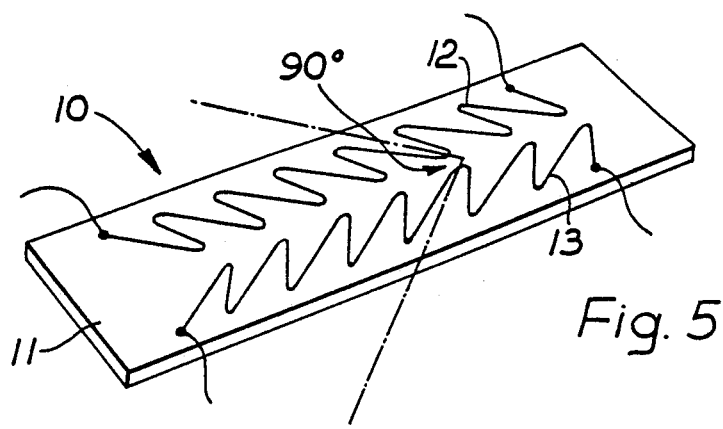
FIG. 5 is a schematic perspective view of an alternative embodiment for measuring shear strain or twisting displacement.

Turning to FIG. 5, the invention also provides a sensor 10 for monitoring twisting movement. A carrier strip 11, similar to that of the previous embodiment, has secured thereto a pair of sepentine strain gauges 12, 13 comprising lengths arranged oblique to the longitudinal axis of the strip 11; preferably the mean angle is 45°. The sensor 10 acts in a manner analogous to the above embodiment to give an output indicative of the relative rotational twist between its ends about the longitudinal axis.

Figure 6:
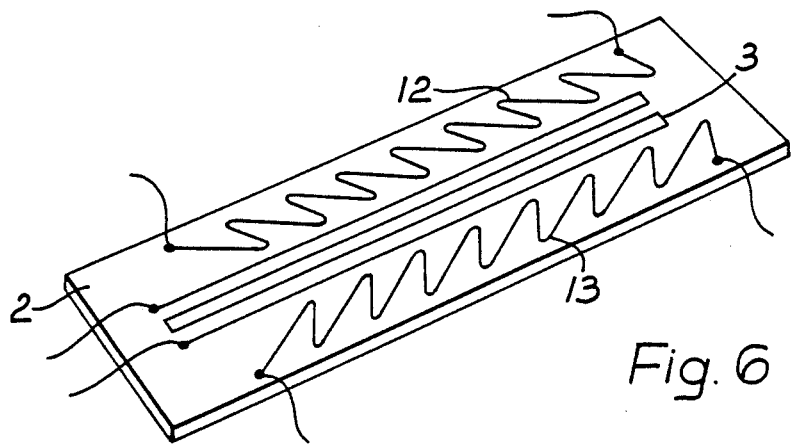
FIG. 6 illustrates a device combining the features of FIGS. 1 and 5.

The embodiments of FIGS. 1 and 5 can be combined as shown in FIG. 6. Such a device provides means for defining the three-dimensional angular orientation of one end of the device relative to the other.

I claim:

1. An electrical sensor for use in providing a signal indicative of angular displacement between two spaced locations, comprising a generally planar flexible carrier of material capable of flexing when its ends are fixed to said locations and said locations undergo relative rotary movement within a predetermined angular range; and at least one electrically conductive element having a resistance which is a function of strain affixed to the carrier and extending therealong substantially the whole distance between said locations; wherein said electrically conductive element comprises a wire resistance strain gauge and the thickness of said carrier is selected such that the strain at the surface thereof does not exceed a predetermined limit when the carrier is flexed by relative rotary movement of said locations within said predetermined angular range, said limit being selected such that there is no permanent plastic deformation of the carrier or the strain gauge when the relative movement of said locations within said predetermined angular range causes maximum flexure of the carrier; and wherein the thickness of the carrier is determined according to the equation:

$$Y = \epsilon R;$$

where Y is half the thickness of the carrier, $\epsilon$ is the maximum permissible strain at the surface thereof, and R is the minimum required radius of curvature of the carrier.

2. The device of claim 1 in which said element comprises one or more conductor tracks located on one face of the carrier and aligned with the longitudinal axis of the carrier.

3. The device of claim 2 including a second element of like form affixed to an opposite face of the carrier.

4. The device of claim 1 comprising two elements affixed to one face of the carrier, each element comprising a serpentine path of sections oblique to the longitudinal axis of the carrier, the oblique orientations of the two elements to said axis being substantially equal and opposite.

5. The device of claim 4 including a third element located on the same face of the carrier as said two elements and comprising one or more conductor tracks aligned with the longitudinal axis of the carrier.

6. The device of claim 5 including a fourth element of like form to said third element and affixed to the opposite face of said carrier.

7. The device of claim 1, 2, 3, 4, 5, or 6 wherein the maximum permissible strain is 1000 microstrain.

8. The device according to any of claims 1, 2, 3, 4, 5, or 6 in which the carrier is capable of flexing without permanent plastic deformation through a radius of curvature of less than 250 mm.

9. The device according to any of claims 1, 2, 3, 4, 5, or 6 in which the carrier is a spring steel strip of thickness 0.5 mm or less.

* * * * *